United States Patent [19]

Nayak

[11] Patent Number: 4,981,785

[45] Date of Patent: Jan. 1, 1991

[54] APPARATUS AND METHOD FOR PERFORMING IMMUNOASSAYS

[75] Inventor: P. Narayan Nayak, Yarmouth, Me.

[73] Assignee: Ventrex Laboratories, Inc., Portland, Me.

[21] Appl. No.: 202,269

[22] Filed: Jun. 6, 1988

[51] Int. Cl.⁵ .................. C12Q 1/00; G01N 33/53
[52] U.S. Cl. ......................... 435/7; 436/514; 436/518; 436/531; 436/807; 436/169; 436/162; 422/56; 422/58; 422/70; 422/102; 422/104; 422/82.05; 422/82.09; 422/82.08; 210/635; 210/638; 210/198.3
[58] Field of Search ............ 435/7; 436/514, 518, 436/531, 807, 169, 162; 422/56, 58, 68, 70, 102, 104; 210/635, 638, 198.3

[56] References Cited

U.S. PATENT DOCUMENTS

| | | | |
|---|---|---|---|
| 3,420,708 | 1/1969 | Schaffer | 127/5 |
| 4,235,601 | 11/1980 | Deutsch | 436/518 X |
| 4,435,504 | 3/1984 | Zuk | 436/530 X |
| 4,446,232 | 5/1984 | Liotta | 422/56 X |
| 4,751,060 | 6/1988 | Kratochwill | 422/268 |

Primary Examiner—Robert A. Wax
Assistant Examiner—Bradley L. Sisson
Attorney, Agent, or Firm—Frederick Cantor

[57] ABSTRACT

An apparatus and method for performing enzyme-linked immunological sandwich assays (ELISA) by affinity chromatography. Formation of the antibody-antigen-conjugate complex, and the development of a chromatophore indicator take place in a semi-automated, walk-away, fashion. The immunoassay apparatus comprises a chromatography tank, which further comprises a reaction compartment and a plurality of liquid solvent reservoirs, with a first-liquid reservoir being configured higher than a second-liquid reservoir. The apparatus allows automatic sequential and discrete movement of wash solution, followed by a color development solution, with unbound conjugate being substantially washed away from the immunological sandwich complex before the color development solution automatically comes into contact with the immunological complex.

8 Claims, 1 Drawing Sheet

APPARATUS AND METHOD FOR PERFORMING IMMUNOASSAYS

BACKGROUND OF THE INVENTION

The present invention relates to an affinity chromatography apparatus and method.

The present invention further relates to a semi-automated apparatus and method for performing immunoassays.

The present invention more particularly relates to an apparatus and method for semi-automatically carrying out enzyme-linked immunological sandwich assays (ELISA), by means of affinity chromatography.

The present invention further relates to an apparatus and method for carrying out "sandwich-type" immunoassays by affinity paper, or other flexible support matrix chromatography, in a semi-automated fashion.

The recent biotechnological development and commercialization of monoclonal antibodies as a source of inexpensive, homogenous immunoglobulins has led to the widespread use of inexpensive, relatively easy to use, immunoassays for a wide variety of antigenic substances found in human and animal body fluids.

In sandwich assays, a sample, which may or may not contain an antigenic subject molecule X, is allowed to react with an anti-X antibody, which anti-X antibody has been previously, either covalently or otherwise, bound to a paper strip or other support matrix. Any subject molecule X in the sample which reacts with the anti-X antibody consequently becomes irreversibly bound to the paper strip or other support matrix.

Next, a conjugate, which is made of the same or another type of anti-X antibody, previously covalently bound to a marker, is allowed to react with the original subject molecule X-anti-X antibody immobilized complex. Any excess free conjugate is then washed away. In this technique, the amount of marker that becomes irreversibly bound to the complex is proportional to the amount of subject molecule X in the sample in question.

The conjugate-bound marker may be either a radioactive isotope, or it may also be an enzyme. A radioactive isotope marker may be readily measured by conventional scintillation counting. A conjugate-bound enzyme marker may be measured by whichever is the preferred way by which the particular enzyme of choice is usually measured. One of the most convenient types of conjugate-bound enzymes to use as a marker for immunoassays is that of colorimetric enzymes, or enzymes that convert a colorless, or near colorless, chromatogen into a strongly-colored, and therefore easily measurable, chromatophore. Additionally, in certain methods, fluorometric markers are also envisioned for use with the apparatus and method of the present invention. Colorimetric enzyme markers are generally easier, safer, and less expensive to use in ELISA than are radioactive markers.

The aforementioned support matrix may be preferably a flexible non-paper porous or non-porous membrane, or a flexible paper strip. In either case, ELISA constitutes a particular type of affinity chromatography.

The above comments are supplied here to provide both a background and rationale for using a colorimetric ELISA affinity chromatography method for the detection of various antigenic protein molecules or non-protein molecules of interest in human or animal body fluids, utilizing the apparatus and method of the present invention.

One of the main problems encountered in utilizing ELISA with the prior art capillary affinity chromatography systems, such as those disclosed in U.S. Pat. No. 4,094,647 by Deutsch and Mead and in U.S. Patent No. 4,690,907, Hibino and Hirato is that ELISA cannot be carried out in such systems in a single semi-automated procedure of the type to which the present invention relates. That is, after a conjugate has reacted in the above prior art systems, and the excess conjugate is washed away, the support matrix must then be physically taken out of the wash solution reservoir, and manually placed into a separate color development solution reservoir. Thus, at least two distinct manual steps or procedures are required in order to perform ELISA in prior art affinity chromatography systems. If these two manual procedures are not carefully and cleanly carried out, or not accurately timed and separated, then false positive and other spurious test results can occur, due in part to the reaction of the color development solution with excess unbound conjugate.

SUMMARY OF THE INVENTION

It is an object of the present invention, to provide both a method and an apparatus for performing immunoassays in which such assays may be accomplished in a "walk-away" fashion, i.e., a semi-automated single procedure.

It is a further object of the present invention to provide both a method, and an apparatus for performing "sandwich-type" immunoassays by affinity chromatography in a semi-automated procedure, utilizing a plurality of sequentially arranged liquid reservoirs configured at different heights, resulting in the sequential and discrete laminar and non-turbulent movement of liquids contacting sample, antigen, antibody, and conjugate, respectively.

These, and other objects of the present invention, are accomplished in accordance with the herein described exemplary embodiment of the apparatus and method of the present invention.

The apparatus preferably comprises a box-like or tank structure containing a plurality of compartments for carrying out paper, or other porous or non-porous support matrix affinity-chromatography, which box-like or tank structure further comprises a plurality of liquid solvent reservoirs, with a first-liquid reservoir being higher elevated than a second-liquid reservoir. The higher elevated first-liquid reservoir receives a wash solution, and the lower elevated second-liquid reservoir receives a color development solution.

The end of the paper strip or support matrix furthest downstream from the wash liquid reservoir is preferably placed in contact with an absorbent pad within an excess fluid reservoir of the apparatus. The other end of the paper strip or support matrix is looped through both the wash solution and color development reservoirs.

In the method of the present invention utilizing the apparatus of the present invention, an antibody to a specific antigenic subject molecule X is applied to a paper strip, or other support matrix, downstream from the wash reservoir, and is either covalently or otherwise bound to the support matrix. Next, also a non-bound conjugate is placed on the paper or support matrix nearer downstream to the wash reservoir. A sample is then placed between the antibody and the conjugate on the paper or support matrix. In one embodiment the support matrix, now containing the conjugate, the antibody, and the sample, is then placed into the reaction compartment of the chromatography apparatus. However, in another embodiment of the present invention, the support matrix may also be placed in the apparatus before the application of the sample, conjugate, and antibody to the support matrix.

The wash solution then automatically, non-turbulently discretely, carries the sample band, first to the location of the antibody band which is bound on the support matrix. The antigenic subject molecule X, if present in the sample, will then bind to the antibody. The wash solution will then, automatically and discretely, carry the conjugate to the location of the antibody-subject molecule X complex, and the conjugate then binds to the antibody-subject molecule X complex. The remaining wash solution will then substantially carry away excess unbound conjugate into the excess fluid reservoir.

When the wash solution is completely drained from its higher situated first-liquid reservoir, the color development solution contained in the lower situated second-liquid reservoir begins to migrate by capillary action along the support matrix. When the color development solution has reached the location of the antibody-subject molecule X-conjugate complex, the enzyme of the conjugate functions to convert a chromatogen found in the color development solution into a measurable chromatophore. The final result is a band or region of measurable color found at the location of the antibody-subject molecule X-conjugate complex, if there was indeed any subject molecule X in the previously introduced sample. If there was no subject X molecule contained in the sample, then no distinct band of color would appear on the support matrix.

An important feature of the present invention resides in the fact that the apparatus and method as described herein, automatically ensures that unbound conjugate will be substantially and cleanly washed away from the immobilized antibody-subject molecule X-conjugate sandwich complex before any color development solution is allowed to react with the immobilized sandwich complex. As a result, false positive and other spurious results which may occur when a color development compound reacts with unbound conjugate are thereby eliminated.

The present invention therefore encompasses, as described in the paragraphs immediately below, the following preferred embodiments:

1. An apparatus and method for semi-automatically performing enzyme-linked immunological sandwich assays (ELISA) in an affinity chromatography apparatus comprising a plurality of liquid reservoir compartments arranged at varying preconfigured heights, resulting in the semi-automatic, sequential, and discrete movement of liquids along a support matrix, on which a sample, an antibody, and a conjugate have been previously applied.

2. An apparatus and method for semi-automatically performing enzyme-linked immunological sandwich assays by affinity chromatography, according to paragraph 1 directly above, wherein said plurality of liquid reservoir compartments arranged at varying preconfigured heights further comprise a lower situated second-liquid reservoir compartment containing a color development solution and a higher elevated first-liquid reservoir compartment containing a wash solution.

3. An apparatus for semi-automatically performing enzyme-linked immunological sandwich assays by affinity chromatography, comprising a chromatography apparatus, defined by panels into a plurality of sequentially arranged compartments, comprising a lower-situated second-liquid reservoir compartment containing a color development solution, a higher-elevated first-liquid reservoir compartment containing a wash solution, a non-liquidfilled reaction compartment, and a third reservoir compartment for accumulation of excess liquids, said pre-configured elevations of said second and first-liquid reservoir compartments resulting in an automatic, sequential, and discretely occurring, laminar, non-turbulent flow of liquids from said second and first-liquid reservoir compartments, respectively, along a prepositioned support matrix placed within said reaction compartment, resulting in immunological reactions between an antibody, sample, and conjugate which have been previously applied to said support matrix, followed as well by a colorimetric reaction, occurring on said support matrix.

4. An apparatus, as described in paragraph 3 directly above, and a method for semi-automatically performing enzyme-linked immunological sandwich assays by affinity chromatography, comprising:
 (a) applying and binding an antibody to a support matrix;
 (b) applying a sample separated from said antibody on said support matrix;
 (c) applying a conjugate separated from said sample and antibody on said support matrix;
 (d) placing said support matrix having said antibody, said sample, and said conjugate applied thereon, either before or after placing said support matrix into a reaction chamber of said chromatography apparatus, such that;
  (i) firstly, a wash solution migrates by capillarity sequentially and discretely along said support matrix, resulting in immunological reactions between said antibody, sample and conjugate; and
  (ii) secondly, a color development solution migrates by capillarity along said support matrix, following the complete previous migration of the wash solution, resulting in a colorimetric reaction produced by certain products of said immunological reactions and said color development solutions.

5. An apparatus for semi-automatically performing enzyme linked immunological sandwich assays by affinity chromatography, according to paragraph 3 above wherein said third reservoir for excess liquids further contains an absorbent pad, said pad being in physical contact with said support matrix.

6. An apparatus as described in paragraph 3 above, and a method for semi-automatically performing enzyme linked immunological sandwich assays of human chorionic gonadotropin (HCG), by affinity chromatography, comprising:
 (a) applying and binding anti-HCG antibody to a support matrix;
 (b) applying a sample, which may contain HCG, being separated from said anti-HCG antibody, on said support matrix;
 (c) applying an anti-HCG antibody-enzyme conjugate, being separated from said sample and said anti-HCG antibody on said support matrix;
 (d) placing said support matrix having said anti-HCG antibody, said sample, and said anti-HCG antibody-enzyme conjugate, applied thereon, either before or after placing said support matrix in a reaction compartment of said chromatographic apparatus, such that;
  (i) firstly a wash solution which migrates sequentially, non-turbulently and discretely along said porous support matrix;
  (ii) secondly, a color development solution which migrates sequentially, non-turbulently and discretely along said support matrix, both wash and color development solutions moving by means of capillary action;
(e) said sequential and discrete movement of said wash solution along said porous support matrix resulting in immunological reactions between said sample, antibody and conjugate;
(f) being then followed by removal of excess sample of said wash solution from said support matrix;
(g) being followed by reaction of said antibody-enzyme conjugate with molecules of HCG immobilized by the antibody;
(h) being followed by removal of excess conjugate from the antibody by said wash solution; and
(i) being followed by reaction of color development solution with products of said immunological reaction, thereby forming colored measurable products.

7. An apparatus and method for semi-automatically performing enzyme-linked immunological sandwich assays by affinity chromatography, according to paragraphs 3, 4, and 6, above, wherein said color development solution contains a colorless, or nearly colorless, chromatogen, which is converted by a conjugate enzyme, or said anti-HCG antibody-enzyme conjugate, into a strongly colored and measurable chromatophore.

8. An apparatus for semi-automatically performing enzyme linked immunological sandwich assays by affinity chromatography, according to paragraph 3 above, further comprising the addition of a self-contained, self-dispensing, cassette-like means, for containing and applying all necessary liquids, reagents, samples, etc., to the support matrix and liquid reservoirs.

BRIEF DESCRIPTION OF THE DRAWING

In order that the present invention may be more fully and readily understood, and that further features thereof may be better appreciated, the invention will now be described by way of example, with reference to the accompanying drawing.

DETAILED DESCRIPTION OF THE PREFERRED EMBODIMENT

Figure 1:
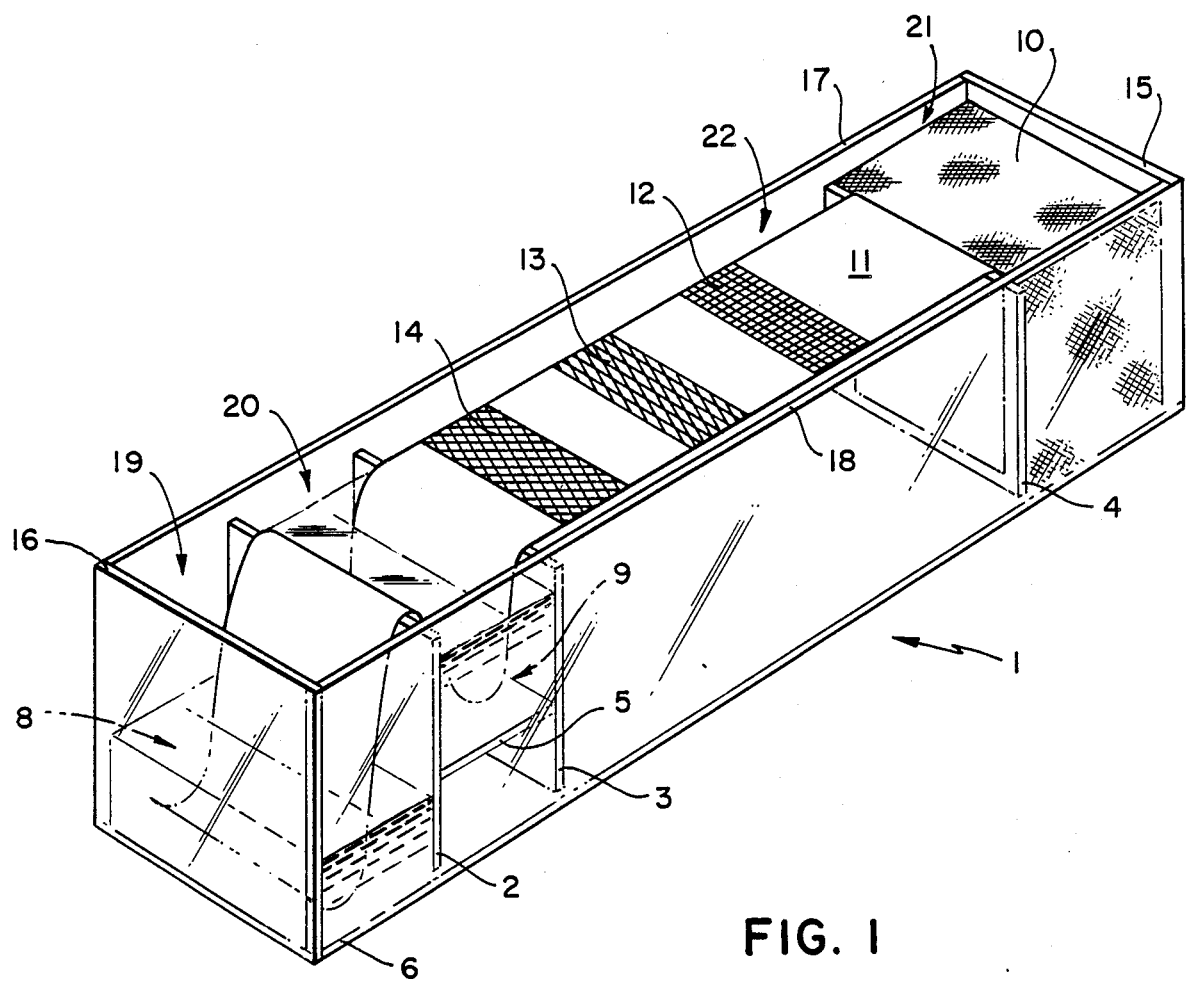
FIG. 1 is an elevated front-facing isometric view of the apparatus for performing immunoassays of the present invention.

Referring now to FIG. 1, which is an elevated front-facing isometric view of the preferred embodiment of the apparatus for performing immunoassays of the present invention.

As seen in FIG. 1, the apparatus for performing immunoassays of the present invention, is depicted generally as 1.

In the preferred embOdiment the apparatus 1 for performing immunoassays takes the form of a rectangularly shaped box-like or tank structure, the housing being preferably comprised of a "plastic" material such as a polystyrene or polyvinyl chloride or the like. The box shaped apparatus 1, is further divided by vertical panel 2, vertical panel 3, and vertical panel 4, into four separate compartments, which will be further described herein. Vertical panels 2, 3, and 4 are preferably recessed below the top of the verticallY oriented housing panels 15, 16, 17, and 18.

The recessing of panels 2, 3, and 4 will also allow the use of a cover panel (not shown) to be placed On top of panels 15, 16, 17, and 18, if desired. A cover panel may aid in maintaining the temperature of the apparatus during its use, and will also prevent environmental contamination. The cover panel may also contain various preconfigured apertures which may be useful, both in the application of and in the viewing of sample, antibody, conjugate, or other substances by a user, carrying out the method of the present invention.

Proceeding sequentially now from the second-liquid reservoir 19 end of the apparatus 1 to the furthest downstream end of the apparatus 1, as shown in FIG. 1, the second-liquid reservoir compartment 19, which is a reservoir for stored liquids, is bounded by panels 16 and 2, and parts of panels 17, 18, and 6, panel 6 being actually the bottom, or floor panel of the apparatus 1.

Next, the first-liquid reservoir compartment 20 which is also a reservoir for stored liquids, is bounded by parts of panels 2, 3, 17, and 18, and further comprises a horizontally-leveled floor panel 5, which is importantly raised above the level of panel 6, i.e., the floor of the second-liquid reservoir compartment 19.

Other liquid reservoirs, in fact, a pluralitY of such liquid storing reservoirs, may also be employed in various embodiments of the present invention, if desired. They will also be arranged at varying levels in accordance with the principles of the present invention embodiment.

Next follows, in the preferred embodiment, a third compartment, the reaction compartment 22, which does not contain liquid and is bounded ©n the sides by panels 17 and 18, and on the bottom by panel 6 and at the ends by panels 3 and 4.

Finally, a fourth compartment, being the third reservoir compartment 21, which serVes here as, and may be referred to as an excess liquid reservoir 21, is defined by vertical panels 15 and 4, and parts of panels 17, 18, and 6.

The preferred method for performing immunoassays within the present invention, and the method which is utilized in conjunction with the apparatus of the present invention as depicted in FIG. 1, will now be described. The method of the present invention is further exemplified by a colorimetric immunoassay for detection of human chorionic gonadotropin (HCG).

A fluid sample, which may or may not contain HCG antigen may be applied as a sample band 13, across the width of an elongated paper strip, or other flexible porous or non-porous support matrix 11, at the location indicated in FIG. 1. An antibody to HCG (anti-HCG antibody) is also be applied as an antibody band 12, across the width of said support matrix 11, and is either covalently or otherwise bonded to the support matrix 11 at the location indicated in FIG. 1.

Anti-HCG antibody, which is covalently bound to a chromatogen substrate enzyme, i.e., the conjugate, may also be applied as a conjugate band 14, across the width of the support matrix 11, at the location also indicated in FIG. 1. This support matrix 11 may also be shaped in various desired configurations.

It is also possible to apply the sample, antibody and conjugate, etc., as discrete separated regions in shapes other than bands along the support matrix. Additionally, envisioned is the use of partially-"split" strips to isolate the applied substances.

Also envisioned, is the use of a self-contained, self-dispensing cassette-like apparatus for containing and applying all necessary liquids, reagents, etc., as an alternative to the individual manual applications of such liquids, reagents, etc., to the support matrix and liquid reservoirs, as described above.

An aqueous buffered wash solution 9, is introduced into the elevated first-liquid reservoir compartment 20 of the immunoassay apparatus. An aqueous buffered color development solution 8 is introduced into the lower-situated second-liquid reservoir compartment 19 of the immunoassay apparatus. The color development solution 8, contains a colorless, or near colorless, chromatogen, which may be converted by means of the enzyme action of the conjugate into a colored, and thereby measurable, chromatophore. It should be noted that the surface level of the color development solution s, in compartment 19, is kept just below the level of the bottom panel 5 of the wash solution 9, contained in compartment 20.

The support matrix 11, with the aforementioned bound anti-HCG antibody band 12, the non-bound sample band 13, and the non-bound conjugate band 14, applied thereon, being located substantially in the upper portion of the reaction compartment 22, of the immunoassay apparatus 1, as depicted in FIG. 1. It should also be noted that the sample, antibody conjugate, etc., may be applied to the support matrix 11, when the support matrix 11 is either in place in the reaction compartment 22, or still outside of the reaction compartment 22. That is, one end, namely the downstream or beginning end of the support matrix 11, is placed at the bottom of the second-liquid reservoir compartment 19, containing the color development solution 8. The next further downstream section of the support matrix 11, is looped over panel 2, and through, and also in contact with, the bottom of the first-liquid reservoir compartment 20, containing the buffered wash solution 9. The next further downstream portion of the support matrix 11, containing the antibody band 12, the sample band 13, and the conjugate band 14, is preferably suspended in air over the tops of panels 3 and 4, defining the outer limits of the third compartment, i.e., the reaction compartment 22 of the immunoassay apparatus.

The end furthest downstream, or tail end, of the support matrix 11, is introduced into the final and fourth compartment, i.e., the third reservoir compartment 21, also being called the excess-solution reservoir 21, of the immunoassay apparatus. An absorbent pad means 10, is preferably placed into the third liquid reservoir compartment 21, such that said absorbent pad 10 is in close physical contact with the tail end of the support matrix 11, thereby evenly facilitating the liquid capillary transport process of the present invention.

The apparatus and method for performing immunoassays, of the present invention, functions as now described. As soon as the properly prepared support matrix 11, containing the desired sample, antibody, conjugate, etc., is in place in the properly prepared immunoassay apparatus 1, the buffered wash solution 9, contained in the higher elevated first-liquid reservoir compartment 20, starts its laminar, non-turbulent flow up and along the support matrix 11, by means of capillary action. The wash solution 9 contacts and transports, cleanly and without mixing, the movable components of the conjugate band 14, and the sample band 13, as two sequentially separated moving bands behind a liquid front, towards the bound antibody band 12.

The first sequentially moving band to encounter the bound antibody band 12 is the sample band 13. Any antigenic HCG present in the sample band 13, becomes firmly attached to the antibody band 12. The next sequentially moving band to encounter the antibody band 12, with its now attached HCG, is the conjugate band 14.

Each molecule of antigenic HCG, which has become immobilized by the antibody now, in turn, immobilizes one or more molecules of conjugate. If no HCG molecules are present in the sample to be immobilized by the antibody, then no conjugate will be immobilized on the support matrix 11.

When the buffered wash solution 9 has completely migrated, by capillary action, out of the first-liquid reservoir compartment 20, thereby washing away from the antibody 12 substantially all excess free conjugate, then, and only then, will the color development solution 8 begin to migrate from the lower-situated second-liquid reservoir compartment 19, along the support matrix 11.

When the color development solution 8 reaches the bound antibody-HCG-conjugate sandwich complex, then the enzyme in the conjugate generates chromatophore from the chromatogen, yielding a colored band which may be measured colorimetrically, thus indicating the amount, if any, of HCG in the sample. After the color development solution 8 has completely migrated by capillary action from the second-liquid reservoir compartment 19, the support matrix 11, is ultimately measured visually or otherwise, to determine the presence and amount of the HCG in the sample. It should also be noted that the occasional presence on the strip of free unbound conjugate gives rise to varying amounts of strip "background" color. It is, therefore, useful to employ both positive and reagent controls in order to eliminate errors in reading of the results of the immunoassay method. The use of "split" strips (i.e., longitudinally partially split) may also be employed when running both controls and several samples on one strip.

The previous detailed description of the preferred embodiment of the present invention is presented for purposes of clarity of understanding only, and no unnecessary limitations should be understood or inferred therefrom, as all appropriate equivalents to the above, which may be obvious to those skilled in the arts pertaining thereto, are considered to be encompassed herein, as an inherent part of the present invention.

What is claimed is:

1. An apparatus for semi-automatically performing enzyme-linked immunological sandwich assays, (ELISA), in an affinity chromatography apparatus, comprising a plurality of liquid reservoir compartments, containing liquids, arranged at varying preconfigured heights, and a support matrix, such that liquids move in a semi-automatic sequential and discrete movement along said support matrix, having previously applied thereon a sample, an antibody and a conjugate.

2. An apparatus for semi-automatically performing enzyme linked immunological sandwich assays by affinity chromatography, according to claim 1, wherein said plurality of liquid reservoir compartments arranged at varying preconfigured heights, further comprises a lower situated second-liquid reservoir compartment, containing a color development solution, and a higher elevated first-liquid reservoir compartment, containing a wash solution.

3. An apparatus for semi-automatically performing enzyme linked immunological sandwich assays by affinity chromatography, comprising a chromatography apparatus, defined by panels into a plurality of sequentially arranged compartments, further comprising a lower-situated second-liquid reservoir compartment, containing a color development solution, and a higher-elevated first-liquid reservoir compartment containing a wash solution, a non-liquid filled reaction compartment, and a third reservoir compartment, for accumulation of excess liquids, said preconfigured elevations of said second and first-liquid reservoir compartments, and a support matrix, such that automatic, sequentially, and discretely occurring, laminar, non-turbulent flow of liquids, occurs, from said second and first-liquid reservoir compartments, along said prepositioned support matrix, placed within said reaction compartment and said first, second, and third liquid reservoir compartments, resulting in immunological reactions between an antibody, bound to said support matrix, sample, and conjugate, previously applied to said support matrix, followed as well by a colorimetric reaction, occurring on said support matrix.

4. A method for semi-automatically performing enzyme linked immunological sandwich assays by affinity chromatography, comprising:
(a) applying and binding an antibody to a discrete location on a support matrix;
(b) applying a sample at a discrete location separate from said antibody on said support matrix;
(c) applying a conjugate at a discrete location separate from said sample and antibody on said support matrix;
(d) placing said support matrix, having said antibody, said sample, and said conjugate, applied thereon, either before or after placing said support matrix into a reaction chamber of a chromatography apparatus, such that;
(e) firstly, a wash solution migrates by capillarity sequentially and discretely along said support matrix, resulting in immunological reactions between said antibody, sample and conjugate; and
(f) secondly, a color development solution migrates by capillarity along said support matrix, following the complete previous migration of the wash solution, resulting in a colorimetric reaction produced by certain products of said immunological reactions and said color development solution.

5. An apparatus for semi-automatically performing enzyme linked immunological sandwich assays by affinity chromatography, according to claim 3, wherein said third reservoir for excess liquids, further contains an absorbent pad, said pad being in physical contact with said support matrix.

6. A method for semi-automatically performing enzyme linked immunological sandwich assays of human chorionic gonadotropin (HCG), by affinity chromatography, comprising:
(a) applying and binding anti-HCG antibody to a discrete location on a support matrix;
(b) applying a sample, which may contain HCG, being at a discrete location separate from said anti-HCG antibody, on said support matrix;
(c) applying an anti-HCG antibody-enzyme conjugate, being at a discrete location separate from said sample and said anti-HCG antibody on said support matrix;
(d) placing said support matrix having said anti-HCG antibody, said sample, and said anti-HCG antibody-enzyme conjugate, applied thereon, either before or after placing said support matrix in a reaction compartment of said chromatographic apparatus, such that; firstly, a wash solution which migrates sequentially, non-turbulently and discretely along said support matrix; followed by, secondly a color development solution which migrates sequentially non-turbulently and discretely along said support matrix, both wash and color development solutions moving by means of capillary action;
(e) said sequential and discrete movement of said wash solution along said support matrix resulting in immunological reactions between said sample, antibody and conjugate;
(f) being then followed by removal of excess sample by said wash solution from said support matrix;
(g) being then followed by reaction of said antibody-enzyme conjugate with molecules of HCG immobilized by the antibody;
(h) being followed by removal of excess conjugate from the antibody by said wash solution; and
(i) being followed by reaction of color development solution with products of said immunological reaction, thereby forming colored measurable products.

7. A method for semi-automatically performing enzyme linked immunological sandwich assays by affinity chromatography, according to claims 3, 4, or 6, wherein said color development solution contains a colorless, or nearly colorless, chromatogen, which is converted by a conjugate enzyme, or said anti-HCG antibody-enzyme conjugate, into a strongly colored and measurable chromatophore.

8. An apparatus for semi-automatically performing enzyme linked immunological sandwich assays by affinity chromatography, according to claims 1, 2, 3 or 5, further comprising the utilization of a self-contained, self-dispensing, cassette-like means for containing and applying all necessary liquids, and reagents, to the support matrix and liquid reservoirs.

* * * * *